(12) United States Patent
Flores et al.

(10) Patent No.: US 8,435,977 B2
(45) Date of Patent: *May 7, 2013

(54) HETEROAROMATIC AND AROMATIC PIPERAZINYL AZETIDINYL AMIDES AS MONOACYLGLYCEROL LIPASE INHIBITORS

(75) Inventors: Chris Flores, Spring House, PA (US); Marina Nelen, Spring House, PA (US); Erica Nulton, Spring House, PA (US); Stephen Prouty, Philadelphia, PA (US); Matthew Todd, Spring House, PA (US); Sui-Po Zhang, Radnor, PA (US)

(73) Assignee: Janssen Pharmaceutica, NV (BE)

( * ) Notice: Subject to any disclaimer, the term of this patent is extended or adjusted under 35 U.S.C. 154(b) by 157 days.

This patent is subject to a terminal disclaimer.

(21) Appl. No.: 12/765,675

(22) Filed: Apr. 22, 2010

(65) Prior Publication Data
US 2010/0324016 A1    Dec. 23, 2010

Related U.S. Application Data

(60) Provisional application No. 61/171,661, filed on Apr. 22, 2009, provisional application No. 61/171,660, filed on Apr. 22, 2009.

(51) Int. Cl.
*A61K 31/496* (2006.01)

(52) U.S. Cl.
USPC ....... 514/210.18; 544/364; 544/368; 544/373

(58) Field of Classification Search .................. None
See application file for complete search history.

(56) References Cited

U.S. PATENT DOCUMENTS

| | | |
|---|---|---|
| 2004/0167224 A1 | 8/2004 | Ozaki et al. |
| 2006/0148844 A1 | 7/2006 | Nakade et al. |
| 2007/0142394 A1 | 6/2007 | Solomon et al. |
| 2007/0293496 A1 | 12/2007 | Ozaki et al. |
| 2009/0269784 A1* | 10/2009 | Grasberger et al. ............ 435/7.4 |
| 2010/0041651 A1 | 2/2010 | Even et al. |

FOREIGN PATENT DOCUMENTS

| | | |
|---|---|---|
| EP | 2180048 A1 | 4/2010 |
| FR | 2915199 A1 | 10/2008 |
| WO | WO 98/37077 A1 | 8/1998 |
| WO | WO 99/19297 A1 | 4/1999 |
| WO | WO 00/63168 A1 | 10/2000 |
| WO | WO 01/77101 A1 | 10/2001 |
| WO | WO 2004/056800 A1 | 7/2004 |
| WO | WO 2006/097175 A1 | 9/2006 |

OTHER PUBLICATIONS

Magrioti et al. Bioorganic & Medicinal Chemistry Letters, vol. 18, p. 5424-5427 (2008).*
International Search Report and Written Opinion, PCT/US2010/032100, dated Jun. 15, 2010, 12 pages.

Benito et al., "Cannabinoid CB2 receptors in human brain inflammation", Brit J Pharmacol, 2008, vol. 153, pp. 277-285.
Ben-Shabat et al.,"An entourage effect: inactive endogenous fatty acid glycerol esters enhance 2-arachidonoyl-glycerol cannabinoid activity", Eur J Pharmacol, 1998, vol. 353, pp. 23-31.
Cavuoto et al.,"The expression of receptors for endocannabinoids in human and rodent skeletal muscle", Biochem Biophys Res Commun, 2007, vol. 364, pp. 105-110.
Cravatt et al.,"The Endogenous Cannabinoid System and Its Role in Nociceptive Behavior", J Neurobiol, 2004, vol. 61, pp. 149-160.
Comelli et al., "The inhibition of monoacylglycerol lipase by URB602 showed an anti-inflammatory and anti-nociceptive effect in a murine model of acute inflammation", Brit J Pharmacol, 2007, vol. 152, pp. 787-794.
Devane et al., "Isolation and Structure of a Brain Constituent That Binds to the Cannabinoid Receptor", Science, 1992, vol. 258, pp. 1946-1949.
Di Marzo et al., "Endocannabinoids: New Targets for Drug Development", Curr Pharm Des, 2000, vol. 6, pp. 1361-1380.
Di Marzo et al., "Endocannabinoids and the Regulation of their levels in Health and Disease", Curr Opin Lipidol, 2007, vol. 18, pp. 129-140.
Dogrul et al., "'Knock-down' of spinal CB1 receptors produces abnormal pain and elevates spinal dynorphin content in mice", Pain, 2002, vol. 100, pp. 203-209.
Guindon et al.,"Cannabinoid CB2 receptors: a therapeutic target for the treatment of inflammatory and neuropathic pain", Brit J Pharmacol, 2008, vol. 153, pp. 319-334.
Hajrasouliha et al., "Endogenous cannabinoids contribute to remote ischemic preconditioning via cannabinoid CB2 receptors in the rat heart", Eur J Pharmacol, 2008, vol. 579, pp. 246-252.
Jhaveri et al., "Endocannabinoid metabolism and uptake: novel targets for neuropathic and inflammatory pain", Brit J Pharmacol, 2007, vol. 152, pp. 624-632.
Kathuria et al., "Modulation of anxiety through blockade of anandamide hydrolysis", Nat Med, 2003, vol. 9, pp. 76-81.
Lichtman et al., "Pharmacological Activity of Fatty Acid Amides Is Regulated, but Not Mediated, by Fatty Acid Amide Hydrolase in Vivo", J Pharmacol Exp Ther, 2002, 302, 73-9.
Lichtman et al., "Mice lacking fatty acid amide hydrolase exhibit a cannabinoid receptor-mediated phenotypic hypoalgesia", Pain, 2004, vol. 109, pp. 319-327.

(Continued)

*Primary Examiner* — Emily Bernhardt

(57) ABSTRACT

Disclosed are compounds, compositions and methods for treating diseases, syndromes, conditions and disorders that are affected by the inhibition of MGL, including pain. Such compounds are represented by Formula (I) as follows:

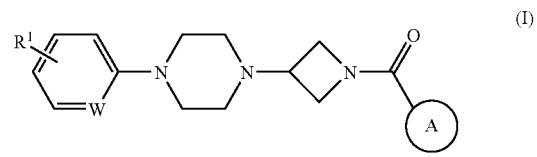

wherein $R^1$, W and

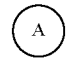

are defined herein.

11 Claims, No Drawings

OTHER PUBLICATIONS

Matsuda et al., "Structure of a Cannabinoid Receptor and Functional Expression of the cloned cDNA", Nature, 1990, vol. 346, pp. 561-564.

Matulis et al, "Thermodynamic Stability of Carbonic Anhydrase: Measurements of Binding Affinity and Stoichiometry Using ThermoFluor", Biochemistry, 2005, vol. 44, pp. 5258-5266.

McCarberg B. et al., "The Future of Cannabinoids as Analgesic Agents: A Pharmacologic, Pharmacokinetic, and Pharmacodynamic Overview", Amer J Ther, 2007, vol. 14, pp. 475-483.

Mechoulam et al., "Identification of an Endogenous 2-Monoglyceride, Present in Canine Gut, that Binds to Cannabinoid Receptors", Biochem Pharmacol, 1995, vol. 50, pp. 83-90.

Munro et al., "Molecular Characterization of a Peripheral Receptor for Cannabinoids", Nature, 1993, vol. 365, pp. 61-65.

Njie, Ya Fatou et al, "Aqueous humor outflow effects of 2-arachidonylglycerol", Exp. Eye Res., 2008, vol. 87(2), pp. 106-114.

Pacher et al., "Pleiotropic effects of the $CB_2$ cannabinoid receptor activation on human monocyte migration: implications for athero sclerosis and inflammatory diseases", Amer J Physiol, 2008, vol. 294, pp. H1133-H1134.

Pantoliano, M. W. et al., "High-Density Miniaturized Thermal Shift Assays as a General Strategy for Drug Discovery", J Biomol Screen, 2001, vol. 6, pp. 429-440.

Pertwee, "The diverse CB1 and CB2 receptor pharmacology of three plant cannabinoids: $\Delta^9$-tetrahydrocannabinol, cannabidiol and $\Delta^9$-tetrahydrocannabivarin", Brit J Pharmacol, 2008, vol. 153, pp. 199-215.

Piomelli, "The Molecular Logic of Endocannabinoid Signalling", Nat Rev Neurosci, 2003, vol. 4, pp. 873-884.

Sugiura et al., "2-Arachidonoylglycerol: A Possible Endogenous Cannabinoid Receptor Ligand in Brain", Biochem Biophys Res Commun, 1995, vol. 215, pp. 89-97.

Walker et al., "Pain modulation by release of the endogenous cannabinoid anandamide", Proc Natl Acad Sci USA, 1999, vol. 96, pp. 12198-12203.

* cited by examiner

HETEROAROMATIC AND AROMATIC PIPERAZINYL AZETIDINYL AMIDES AS MONOACYLGLYCEROL LIPASE INHIBITORS

CROSS REFERENCE TO RELATED APPLICATIONS

This application claims the benefit of U.S. Provisional Application No. 61/171,661, filed on Apr. 22, 2009, which is incorporated by reference herein in its entirety.

This application is related to provisional application entitled, Heteroaromatic and Aromatic Piperazinyl Azetidinyl Amides as Monoacylglycerol Lipase Inhibitors, filed on Apr. 22, 2009, U.S. provisional patent application Ser. No. 61/171,660.

STATEMENT REGARDING FEDERALLY SPONSORED RESEARCH OR DEVELOPMENT

The research and development of the invention described below was not federally sponsored.

FIELD OF THE INVENTION

The present invention is directed to the use of a compound of formula (I) as herein defined for the treatment, amelioration and/or prevention of an MGL disorder in a subject, including a mammal and/or human, in which the disease, syndrome, or condition is affected by MGL.

BACKGROUND OF THE INVENTION

*Cannabis sativa* has been used for the treatment of pain for many years. $\Delta^9$-tetrahydrocannabinol is a major active ingredient from *Cannabis sativa* and an agonist of cannabinoid receptors (Pertwee, *Brit J Pharmacol*, 2008, 153, 199-215). Two cannabinoid G protein-coupled receptors have been cloned, cannabinoid receptor type 1 ($CB_1$, Matsuda et al., *Nature*, 1990, 346, 561-4) and cannabinoid receptor type 2 ($CB_2$, Munro et al., *Nature*, 1993, 365, 61-5). $CB_1$ is expressed centrally in brain areas, such as the hypothalamus and nucleus accumbens, as well as peripherally in the liver, gastrointestinal tract, pancreas, adipose tissue and skeletal muscle (Di Marzo et al., *Curr Opin Lipidol*, 2007, 18, 129-140). $CB_2$ is predominantly expressed in immune cells, such as monocytes (Pacher et al., *Amer J Physiol*, 2008, 294, H1133-H1134), and, under certain conditions, also in the brain (Benito et al., *Brit J Pharmacol*, 2008, 153, 277-285) and in skeletal (Cavuoto et al., *Biochem Biophys Res Commun*, 2007, 364, 105-110) and cardiac (Hajrasouliha et al., *Eur J Pharmacol*, 2008, 579, 246-252) muscle. An abundance of pharmacological, anatomical and electrophysiological data, using synthetic agonists, indicate that increased cannabinoid signaling through $CB_1/CB_2$ promotes analgesia in tests of acute nociception and suppresses hyperalgesia and/or allodynia in models of chronic neuropathic and inflammatory pain (Cravatt et al., *J Neurobiol*, 2004, 61, 149-60; Guindon et al., *Brit J Pharmacol*, 2008, 153, 319-334).

Efficacy of synthetic cannabanoid receptor agonists is well documented. Moreover, studies using cannabinoid receptor antagonists and knockout mice have also implicated the endocannabinoid system as an important modulator of nociception. Anandamide (AEA) (Devane et al., *Science*, 1992, 258, 1946-9) and 2-arachidinoylglycerol (2-AG) (Mechoulam et al., *Biochem Pharmacol*, 1995, 50, 83-90; Sugiura et al., *Biochem Biophys Res Commun*, 1995, 215, 89-97) are two major endocannabinoids. AEA is hydrolyzed by fatty acid amide hydrolase (FAAH) and 2-AG is hydrolyzed by monoacylglycerol lipase (MGL) (Piomelli, *Nat Rev Neurosci*, 2003, 4, 873-884). Genetic ablation of FAAH elevates endogenous AEA and results in a $CB_1$-dependent analgesia in models of acute and inflammatory pain (Lichtman et al., *Pain*, 2004, 109, 319-27), suggesting that the endocannabinoid system functions naturally to inhibit nociception (Cravatt et al., *J Neurobiol*, 2004, 61, 149-60). Unlike the constitutive increase in endocannabinoid levels using FAAH knockout mice, use of specific FAAH inhibitors transiently elevates AEA levels and results in antinociception in vivo (Kathuria et al., *Nat Med*, 2003, 9, 76-81). Further evidence for an endocannabinoid-mediated antinociceptive tone is demonstrated by the formation of AEA in the periaqueductal gray, a known pain center, following noxious stimulation in the periphery (Walker et al., *Proc Natl Acad Sci USA*, 1999, 96, 12198-203) and, conversely, by the induction of hyperalgesia following the administration of $CB_1$ antisense RNA in the spinal cord (Dogrul et al., *Pain*, 2002, 100, 203-9).

With respect to 2-AG, intravenous delivery produces analgesia in the tail flick (Mechoulam et al., *Biochem Pharmacol*, 1995, 50, 83-90) and hot plate (Lichtman et al., *J Pharmacol Exp Ther*, 2002, 302, 73-9) assays. In contrast, it was demonstrated that 2-AG given alone is not analgesic in the hot plate assay, but when combined with other 2-monoacylglycerols (i.e., 2-linoleoyl glycerol and 2-palmitoyl glycerol), significant analgesia is attained, a phenomenon known as the "entourage effect" (Ben-Shabat et al., *Eur J Pharmacol*, 1998, 353, 23-31). These "entourage" 2-monoacylglycerols are endogenous lipids that are co-released with 2-AG and potentiate endocannabinoid signaling, in part, by inhibiting 2-AG breakdown, most likely by competition for the active site on MGL. This suggests that synthetic MGL inhibitors will have a similar effect. Indeed, URB602, a relatively weak synthetic MGL inhibitor, showed an antinociceptive effect in a murine model of acute inflammation (Comelli et al., *Brit J Pharmacol*, 2007, 152, 787-794).

Although the use of synthetic cannabinoid agonists have conclusively demonstrated that increased cannabinoid signaling produces analgesic and anti-inflammatory effects, it has been difficult to separate these beneficial effects from the unwanted side effects of these compounds. An alternative approach is to enhance the signaling of the endocannabinoid system by elevating the level of 2-AG, the endocannabinoid of highest abundance in the central nervous system (CNS) and gastrointestinal tract, which may be achieved by inhibition of MGL. Therefore, MGL inhibitors are potentially useful for the treatment of pain, inflammation and CNS disorders (Di Marzo et al., *Curr Pharm Des*, 2000, 6, 1361-80; Jhaveri et al., *Brit J Pharmacol*, 2007, 152, 624-632; McCarberg Bill et al., *Amer J Ther*, 2007, 14, 475-83), as well as glaucoma and disease states arising from elevated intraocular pressure (Njie, Ya Fatou; He, Fang; Qiao, Xhuanhong; Song, Zhoa-Hui, *Exp. Eye Res.*, 2008, 87(2):106-14).

SUMMARY OF THE INVENTION

The present invention is directed to a method for treating, ameliorating or preventing a disease, syndrome, condition or disorder that is affected by the inhibition of MGL (such as pain, the diseases that lead to such pain, inflammation and CNS disorders) comprising, consisting of and/or consisting essentially of administering to a subject in need thereof, a therapeutically effective amount of a compound of Formula (I)

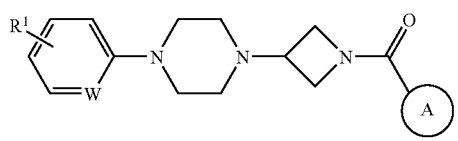 (I)

selected from the group consisting of
a compound wherein W is N, $R^1$ is H,

is

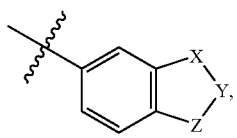

X—Y—Z is —CH—C($R^2$)—N($R^3$)—, $R^2$ is phenoxymethyl, and $R^3$ is 2,2-dimethylpropyl;
a compound wherein W is N, $R^1$ is H,

is

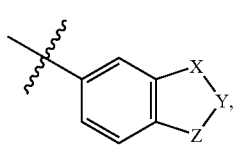

X—Y—Z is —O—C($R^2$)=N—, and $R^2$ is cyclohexyl;
a compound wherein W is N, $R^1$ is H,

is

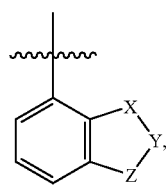

X—Y—Z is —O—C($R^2$)=N—, and $R^2$ is 3-fluorophenyl;

a compound wherein W is N, $R^1$ is H,

is

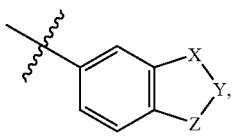

X—Y—Z is —CH—C($R^2$)—N($R^3$)—, $R^2$ is 4-methylphenyl, and $R^3$ is isobutyl;
a compound wherein W is N, $R^1$ is H,

is

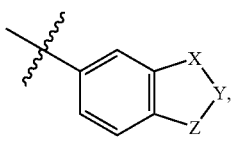

X—Y—Z is —CH—C($R^2$)—N($R^3$)—, $R^2$ is phenylmethyl, and $R^3$ is isobutyl;
a compound wherein W is N, $R^1$ is H,

is

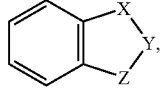

X—Y—Z is —O—C($R^2$)=N—, and $R^2$ is 4-fluorophenyl;
a compound wherein W is N, $R^1$ is H,

is

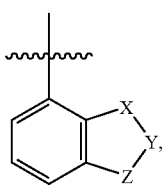

X—Y—Z is —O—C(R$^2$)=N—, and R$^2$ is 4-methoxyphenyl;

a compound wherein W is N, R$^1$ is H,

is

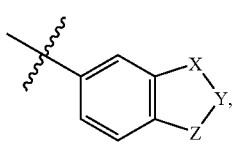

X—Y—Z is —CH=C(R$^2$)—N(R$^3$)—, R$^2$ is isobutyl, and R$^3$ is isobutyl;

a compound wherein W is N, R$^1$ is H,

is

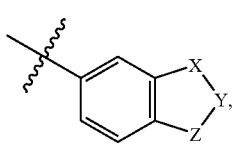

X—Y—Z is —CH=C(R$^2$)—N(R$^3$)—, R$^2$ is phenoxymethyl, and R$^3$ is isobutyl;

a compound wherein W is N, R$^1$ is H,

is

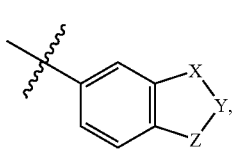

X—Y—Z is —CH=C(R$^2$)—N(R$^3$)—, R$^2$ is phenyl, and R$^3$ is 2,2-dimethylpropyl;

a compound wherein W is N, R$^1$ is H,

is

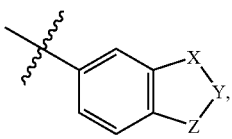

X—Y—Z is —CH=C(R$^2$)—N(R$^3$)—, R$^2$ is phenoxymethyl, and R$^3$ is cyclohexylmethyl;

a compound wherein W is N, R$^1$ is H,

is

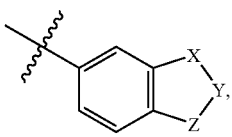

X—Y—Z is —CH=C(R$^2$)—N(R$^3$)—, R$^2$ is cyclopentylmethyl, and R$^3$ is methyl;

a compound wherein W is N, R$^1$ is H,

is

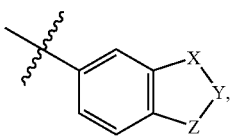

X—Y—Z is —CH=C(R$^2$)—N(R$^3$)—, R$^2$ is phenyl, and R$^3$ is isobutyl;

a compound wherein W is N, R$^1$ is H,

is

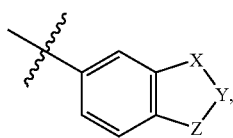

X—Y—Z is —CH=C(R²)—N(R³)—, R² is cyclohexylmethyl, and R³ is hydrogen;
a compound wherein W is N, R¹ is H,

is

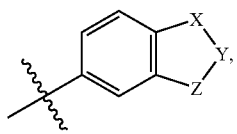

X—Y—Z is —O—C(R²)=N—, and R² is 2-methoxyphenylmethyl;
a compound wherein W si N, R¹ is H,

is

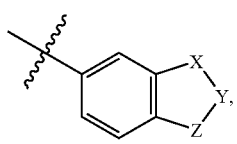

X—Y—Z is —CH=C(R²)—N(R³)—, R² is n-propyl, and R³ is methyl;
a compound wherein W is CH, R¹ is 2-methoxy,

is

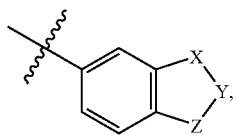

X—Y—Z is —CH=C(R²)—N(R³)—, R² is phenoxymethyl, and R³ is isobutyl;

a compound wherein W is N, R¹ is H,

is

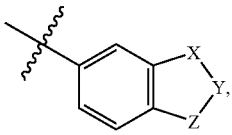

X—Y—Z is —CH=C(R²)—N(R³)—, R² is phenylmethyl, and R³ is cyclohexylmethyl;
a compound wherein W is N, R¹ is H,

is

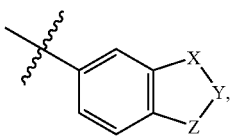

X—Y—Z is —O—C(R²)=N—, and R² is t-butyl;
a compound wherein W is N, R¹ is H,

is

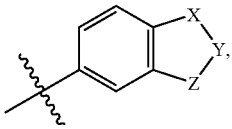

X—Y—Z is —O—C(R²)=N—, and R² is 3-methoxyphenyl;
a compound wherein W is CH, R¹ is 2-methoxy,

is

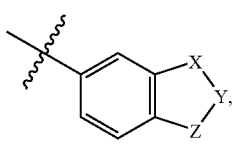

X—Y—Z is —CH—C(R²)—N(R³)—, R² is phenylmethyl, and R³ is isobutyl;

a compound wherein W is CH, R¹ is 2-methoxy,

A is

X—Y—Z is —CH—C(R²)—N(R³)—, R² is phenoxymethyl, and R³ is 2,2-dimethylpropyl;

a compound wherein W is CH, R¹ is 2-methoxy,

A is

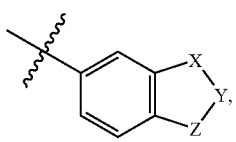

X—Y—Z is —CH—C(R²)—N(R³)—, R² is phenylmethyl, and R³ is cyclohexylmethyl;

a compound wherein W is CH, R¹ is 2-methoxy,

A is

X—Y—Z is —CH—C(R²)—N(R³)—, R² is phenyl, and R³ is 2,2-dimethylpropyl;

a compound wherein W is CH, R¹ is 4-fluoro,

A is

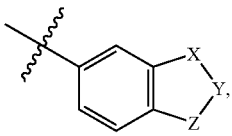

X—Y—Z is —CH—C(R²)—N(R³)—, R² is phenyl, and R³ is 2,2-dimethylpropyl;

a compound wherein W is N, R¹ is H,

A is

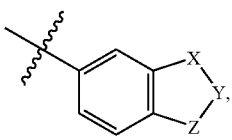

X—Y—Z is —CH—C(R²)—N(R³)—, R² is t-butyl, and R³ is 2,2-dimethylpropyl;

a compound wherein W is N, R¹ is H,

A is

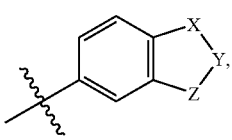

X—Y—Z is —NH—C(R²)—C(R³)—, R² is 4-methylphenyl and R³ is methoxy-methyl-carbonyl;

a compound wherein W is N, R¹ is H,

A is

is

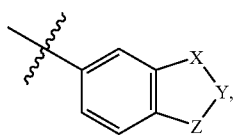

X—Y—Z is —CH—C(R²)—N(R³), R² is n-propyl and R³ is cyclohexylmethyl;

and enantiomers, diastereomers, solvates and pharmaceutically acceptable salts thereof.

The present invention is further directed to the use of a compound of formula (I) as herein defined, for the preparation of a medicament or pharmaceutical composition for the treatment, amelioration or prevention of a disease, syndrome, condition or disorder that is affected by the inhibition of MGL, in a subject in need thereof.

DETAILED DESCRIPTION OF THE INVENTION

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

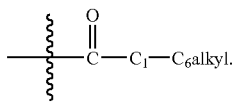

Unless otherwise noted, it is intended that the definition of any substituent or variable at a particular location in a molecule be independent of its definitions elsewhere in that molecule. It is understood that substituents and substitution patterns on the compounds of formula (I) can be selected by one of ordinary skill in the art to provide compounds that are chemically stable and that can be readily synthesized by techniques known in the art as well as those methods set forth herein.

The term "subject" as used herein, refers to an animal, preferably a mammal, most preferably a human, who has been the object of treatment, observation or experiment.

The term "therapeutically effective amount" as used herein, refers to an amount of an active compound or pharmaceutical agent that elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

As used herein, the term "composition" is intended to encompass a product comprising the specified ingredients in therapeutically effective amounts, as well as any product that results, directly or indirectly, from combinations of the specified ingredients in the specified amounts.

As used herein, unless otherwise noted, the terms "treating", "treatment", "ameliorating" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the terms "preventing" and "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical professional to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "MGL inhibitor" is intended to encompass a compound that interacts with MGL to substantially reduce or eliminate its catalytic activity, thereby increasing the concentrations of its substrate(s). The term "MGL-modulated" is used to refer to the condition of being affected by the modulation of the MGL enzyme including the condition of being affected by the inhibition of the MGL enzyme, such as, for example, pain and the diseases that lead to such pain, inflammation and CNS disorders.

As used herein, unless otherwise noted, the term "affect" or "affected" (when referring to a disease, syndrome, condition or disorder that is affected by inhibition of MGL) shall imply a reduction in the frequency and/or severity of one or more symptoms or manifestations of said disease, syndrome, condition or disorder; and/or imply the prevention of the development of one or more symptoms or manifestations of said disease, syndrome, condition or disorder or the development of the disease, condition, syndrome or disorder.

The compounds of formula (I) are useful in methods for treating, ameliorating and/or preventing a disease, a syndrome, a condition or a disorder that is affected by the inhibition of MGL. Such methods comprise, consist of and/or consist essentially of administering to a subject, including an animal, a mammal, and a human in need of such treatment, amelioration and/or prevention, a therapeutically effective amount of a compound of formula (I), or an enantiomer, diastereomer, solvate or pharmaceutically acceptable salt thereof. In particular, the compounds of formula (I) are useful for treating, ameliorating and/or preventing pain; diseases, syndromes, conditions, or disorders causing such pain; inflammation and/or CNS disorders. More particularly, the compounds of formula (I) are useful for treating, ameliorating and/or preventing inflammatory pain, inflammatory hypersensitivity conditions and/or neuropathic pain, comprising administering to a subject in need thereof a therapeutically effective amount of a compound of formula (I), as herein defined.

Examples of inflammatory pain include pain due to a disease, condition, syndrome, disorder, or a pain state including inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain due to physical trauma, headache, sinus headache, tension headache, or arachnoiditis.

One type of inflammatory pain is inflammatory hyperalgesia/hypersensitivity. Examples of inflammatory hyperalgesia include a disease, syndrome, condition, disorder, or pain state including inflammation, osteoarthritis, rheumatoid arthritis, back pain, joint pain, abdominal pain, musculoskeletal diseases, skin diseases, post operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, inflammatory bowel diseases including Crohn's Disease, ulcerative colitis, urinary incontinence, benign prostatic hypertrophy, cough, asthma, rhinitis, nasal hypersensitivity, itch, contact dermititis and/or dermal allegy and chronic obstructive pulmonary disease.

In an embodiment, the present invention is directed to a method for treating, ameliorating and/or preventing inflammatory visceral hyperalgesia in which a enhanced visceral irritability exists, comprising, consisting of, and/or consisting essentially of the step of administering to a subject in need of such treatment a therapeutically effective amount of a compound, salt or solvate of formula (I). In a further embodiment, the present invention is directed to a method for treating inflammatory somatic hyperalgesia in which a hypersensitivity to thermal, mechanical and/or chemical stimuli exists, comprising administering to a mammal in need of such treatment a therapeutically effective amount of a compound of formula (I) or an enantiomer, diastereomer, solvate or pharmaceutically acceptable salt thereof.

A further embodiment of the present invention is directed to a method for treating, ameliorating and/or preventing neuropathic pain. Examples of a neuropathic pain include pain due to a disease, syndrome, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, postherpetic neuralgia, causalgia, red neuralgia, Sluder's neuralgia, splenopalatine neuralgia, supraorbital neuralgia, trigeminal neuralgia, vulvodynia, or vidian neuralgia.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, syndrome, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

In a further embodiment, the present invention is directed to a method for treating, ameliorating and/or preventing neuropathic cold allodynia in which a hypersensitivity to a cooling stimuli exists, comprising, consisting of, and/or consisting essentially of the step of administering to a subject in need of such treatment a therapeutically effective amount of a compound of formula (I) or an enantiomer, diastereomer, solvate or pharmaceutically acceptable salt thereof.

In a further embodiment, the present invention is directed to a method for treating, ameliorating and/or preventing CNS disorders. Examples of CNS disorders include anxieties, such as social anxiety, post-traumatic stress disorder, phobias, social phobia, special phobias, panic disorder, obsessive-compulsive disorder, acute stress, disorder, separation anxiety disorder, and generalized anxiety disorder, as well as depression, such as major depression, bipolar disorder, seasonal affective disorder, post natal depression, manic depression, and bipolar depression.

The present invention is directed to methods of treating, ameliorating and/or preventing a disorder, syndrome, condition or disease that is affected by the inhibition of MGL, comprising, consisting of or consisting essentially of administering to a subject in need thereof a therapeutically effective amount of a compound of formula (I)

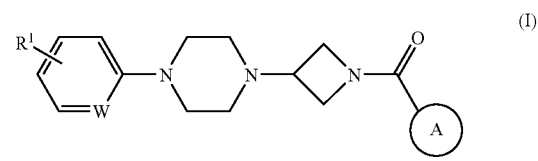

selected from the group consisting of
[1-(2,2-Dimethyl-propyl)-2-phenoxymethyl-1H-indol-5-yl]-[3-(4-pyridin-2-yl-piperazin-1-yl)-azetidin-1-yl]-methanone; (Compound #1)
(2-Cyclohexyl-benzooxazol-6-yl)-[3-(4-pyridin-2-yl-piperazin-1-yl)-azetidin-1-yl]-methanone; (Compound #2)
[2-(3-Fluoro-phenyl)-benzooxazol-7-yl]-[3-(4-pyridin-2-yl-piperazin-1-yl)-azetidin-1-yl]-methanone; (Compound #3)
(1-Isobutyl-2-p-tolyl-1H-indol-5-yl)-[3-(4-pyridin-2-yl-piperazin-1-yl)-azetidin-1-yl]-methanone; (Compound #4)
[1-Isobutyl-2-(4-methyl-benzyl)-1H-indol-5-yl]-[3-(4-pyridin-2-yl-piperazin-1-yl)-azetidin-1-yl]-methanone; (Compound #5)
[2-(4-Fluoro-phenyl)-benzooxazol-7-yl]-[3-(4-pyridin-2-yl-piperazin-1-yl)-azetidin-1-yl]-methanone; (Compound #6)
[2-(4-Methoxy-phenyl)-benzooxazol-7-yl]-[3-(4-pyridin-2-yl-piperazin-1-yl)-azetidin-1-yl]-methanone; (Compound #7)

(1,2-Diisobutyl-1H-indol-5-yl)-[3-(4-pyridin-2-yl-piperazin-1-yl)-azetidin-1-yl]-methanone; (Compound #8)
(1-Isobutyl-2-phenoxymethyl-1H-indol-5-yl)-[3-(4-pyridin-2-yl-piperazin-1-yl)-azetidin-1-yl]-methanone; (Compound #9)
[1-(2,2-Dimethyl-propyl)-2-phenyl-1H-indol-5-yl]-[3-(4-pyridin-2-yl-piperazin-1-yl)-azetidin-1-yl]-methanone; (Compound #10)
(1-Cyclohexylmethyl-2-phenoxymethyl-1H-indol-5-yl)-[3-(4-pyridin-2-yl-piperazin-1-yl)-azetidin-1-yl]-methanone; (Compound #11)
(2-Cyclopentylmethyl-1-methyl-1H-indol-5-yl)-[3-(4-pyridin-2-yl-piperazin-1-yl)-azetidin-1-yl]-methanone; (Compound #12)
(1-Isobutyl-2-phenyl-1H-indol-5-yl)-[3-(4-pyridin-2-yl-piperazin-1-yl)-azetidin-1-yl]-methanone; (Compound #13)
(2-Cyclohexylmethyl-1H-indol-5-yl)-[3-(4-pyridin-2-yl-piperazin-1-yl)-azetidin-1-yl]-methanone; (Compound #14)
[2-(2-Methoxy-benzyl)-benzooxazol-5-yl]-[3-(4-pyridin-2-yl-piperazin-1-yl)-azetidin-1-yl]-methanone; (Compound #15)
(2-Ethyl-1-methyl-1H-indol-5-yl)-[3-(4-pyridin-2-yl-piperazin-1-yl)-azetidin-1-yl]-methanone; (Compound #16)
(1-Isobutyl-2-phenoxymethyl-1H-indol-5-yl)-{3-[4-(2-methoxy-phenyl)-piperazin-1-yl]-azetidin-1-yl}-methanone; (Compound #17)
(2-Benzyl-1-cyclohexylmethyl-1H-indol-5-yl)-[3-(4-pyridin-2-yl-piperazin-1-yl)-azetidin-1-yl]-methanone; (Compound #18)
(2-tert-Butyl-benzooxazol-6-yl)-[3-(4-pyridin-2-yl-piperazin-1-yl)-azetidin-1-yl]-methanone; (Compound #19)
[2-(3-Methoxy-phenyl)-benzooxazol-5-yl]-[3-(4-pyridin-2-yl-piperazin-1-yl)-azetidin-1-yl]-methanone; (Compound #20)
(2-Benzyl-1-isobutyl-1H-indol-5-yl)-{3-[4-(2-methoxy-phenyl)-piperazin-1-yl]-azetidin-1-yl}-methanone; (Compound #21)
[1-(2,2-Dimethyl-propyl)-2-phenoxymethyl-1H-indol-5-yl]-{3-[4-(2-methoxy-phenyl)-piperazin-1-yl]-azetidin-1-yl}-methanone; (Compound #22)
(2-Benzyl-1-cyclohexylmethyl-1H-indol-5-yl)-{3-[4-(2-methoxy-phenyl)-piperazin-1-yl]-azetidin-1-yl}-methanone; (Compound #23)
[1-(2,2-Dimethyl-propyl)-2-phenyl-1H-indol-5-yl]-{3-[4-(2-methoxy-phenyl)-piperazin-1-yl]-azetidin-1-yl}-methanone; (Compound #24)
[1-(2,2-Dimethyl-propyl)-2-phenyl-1H-indol-5-yl]-{3-[4-(4-fluoro-phenyl)-piperazin-1-yl]-azetidin-1-yl}-methanone; (Compound #25)
[2-tert-Butyl-1-(2,2-dimethyl-propyl)-1H-indol-5-yl]-[3-(4-pyridin-2-yl-piperazin-1-yl)-azetidin-1-yl]-methanone; (Compound #26)
2-Methoxy-1-{5-[3-(4-pyridin-2-yl-piperazin-1-yl)-azetidine-1-carbonyl]-2-p-tolyl-1H-indol-3-yl}-ethanone; (Compound #27)
(1-Cyclohexylmethyl-2-propyl-1H-indol-5-yl)-[3-(4-pyridin-2-yl-piperazin-1-yl)-azetidin-1-yl]-methanone; (Compound #28)

and enantiomers, diastereomers, solvates and pharmaceutically acceptable salts thereof. Preferably, the disease, syndrome, condition or disorder that is affected by inhibition of MGL is selected from the group consisting of pain, inflammatory pain, inflammatory hypersensitivity conditions and neuropathic pain, as herein defined.

In an embodiment, the present invention is directed to treating, ameliorating or preventing a disease, syndrome, condition or disorder that is affected by inhibition of MGL, comprising administering to a subject in need thereof, a therapeutically effective amount of a compound of formula (Ia)

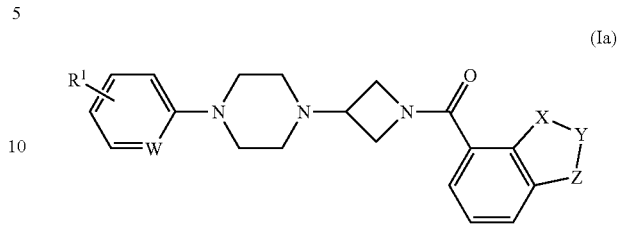

(Ia)

or an enantiomer, diastereomer, solvate or pharmaceutically acceptable salt thereof, wherein $R^1$, W, and —X—Y—Z— are as herein defined. In another embodiment, the present invention is directed to treating, ameliorating or preventing a disease, syndrome, condition or disorder that is affected by inhibition of MGL, comprising administering to a subject in need thereof, a therapeutically effective amount of a compound of formula (Ib)

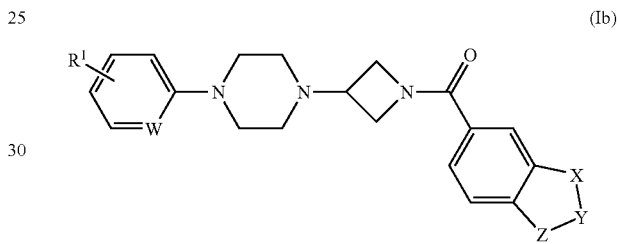

(Ib)

or an enantiomer, diastereomer, solvate or pharmaceutically acceptable salt thereof, wherein $R^1$, W, and —X—Y—Z— are as herein defined. In yet another embodiment, the present invention is directed to treating, ameliorating or preventing a disease, syndrome, condition or disorder that is affected by inhibition of MGL, comprising administering to a subject in need thereof, a therapeutically effective amount of a compound of formula (Ic)

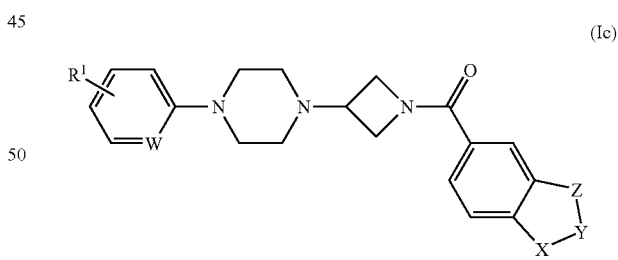

(Ic)

or an enantiomer, diastereomer, solvate or pharmaceutically acceptable salt thereof, wherein $R^1$, W, and —X—Y—Z— are as herein defined.

In another embodiment, the present invention is directed to treating, ameliorating or preventing a disease, syndrome, condition or disorder that is affected by inhibition of MGL, comprising administering to a subject in need thereof, a therapeutically effective amount of a compound selected from the group consisting of

[1-(2,2-Dimethyl-propyl)-2-phenoxymethyl-1H-indol-5-yl]-[3-(4-pyridin-2-yl-piperazin-1-yl)-azetidin-1-yl]-methanone; (Compound #1)

(2-Cyclohexyl-benzooxazol-6-yl)-[3-(4-pyridin-2-yl-piperazin-1-yl)-azetidin-1-yl]-methanone; (Compound #2)

[2-(3-Fluoro-phenyl)-benzooxazol-7-yl]-[3-(4-pyridin-2-yl-piperazin-1-yl)-azetidin-1-yl]-methanone; (Compound #3)

(1-Isobutyl-2-p-tolyl-1H-indol-5-yl)-[3-(4-pyridin-2-yl-piperazin-1-yl)-azetidin-1-yl]-methanone; (Compound #4)

[1-Isobutyl-2-(4-methyl-benzyl)-1H-indol-5-yl]-[3-(4-pyridin-2-yl-piperazin-1-yl)-azetidin-1-yl]-methanone; (Compound #5)

[2-(4-Fluoro-phenyl)-benzooxazol-7-yl]-[3-(4-pyridin-2-yl-piperazin-1-yl)-azetidin-1-yl]-methanone; (Compound #6)

[2-(4-Methoxy-phenyl)-benzooxazol-7-yl]-[3-(4-pyridin-2-yl-piperazin-1-yl)-azetidin-1-yl]-methanone; (Compound #7)

(1,2-Diisobutyl-1H-indol-5-yl)-[3-(4-pyridin-2-yl-piperazin-1-yl)-azetidin-1-yl]-methanone; (Compound #8)

(1-Isobutyl-2-phenoxymethyl-1H-indol-5-yl)-[3-(4-pyridin-2-yl-piperazin-1-yl)-azetidin-1-yl]-methanone; (Compound #9)

[1-(2,2-Dimethyl-propyl)-2-phenyl-1H-indol-5-yl]-[3-(4-pyridin-2-yl-piperazin-1-yl)-azetidin-1-yl]-methanone; (Compound #10)

(1-Cyclohexylmethyl-2-phenoxymethyl-1H-indol-5-yl)-[3-(4-pyridin-2-yl-piperazin-1-yl)-azetidin-1-yl]-methanone; (Compound #11)

(2-Cyclopentylmethyl-1-methyl-1H-indol-5-yl)-[3-(4-pyridin-2-yl-piperazin-1-yl)-azetidin-1-yl]-methanone; (Compound #12)

(1-Isobutyl-2-phenyl-1H-indol-5-yl)-[3-(4-pyridin-2-yl-piperazin-1-yl)-azetidin-1-yl]-methanone; (Compound #13)

(2-Cyclohexylmethyl-1H-indol-5-yl)-[3-(4-pyridin-2-yl-piperazin-1-yl)-azetidin-1-yl]-methanone; (Compound #14)

[2-(2-Methoxy-benzyl)-benzooxazol-5-yl]-[3-(4-pyridin-2-yl-piperazin-1-yl)-azetidin-1-yl]-methanone; (Compound #15)

(2-Ethyl-1-methyl-1H-indol-5-yl)-[3-(4-pyridin-2-yl-piperazin-1-yl)-azetidin-1-yl]-methanone; (Compound #16)

(1-Isobutyl-2-phenoxymethyl-1H-indol-5-yl)-{3-[4-(2-methoxy-phenyl)-piperazin-1-yl]-azetidin-1-yl}-methanone; (Compound #17)

(2-Benzyl-1-cyclohexylmethyl-1H-indol-5-yl)-[3-(4-pyridin-2-yl-piperazin-1-yl)-azetidin-1-yl]-methanone; (Compound #18)

and enantiomers, diastereomers, solvates and pharmaceutically acceptable salt thereof.

In another embodiment, the present invention is directed to the use of a compound selected from the group consisting of

[1-(2,2-Dimethyl-propyl)-2-phenoxymethyl-1H-indol-5-yl]-[3-(4-pyridin-2-yl-piperazin-1-yl)-azetidin-1-yl]-methanone; (Compound #1)

[2-(3-Fluoro-phenyl)-benzooxazol-7-yl]-[3-(4-pyridin-2-yl-piperazin-1-yl)-azetidin-1-yl]-methanone; (Compound #3)

(1-Isobutyl-2-p-tolyl-1H-indol-5-yl)-[3-(4-pyridin-2-yl-piperazin-1-yl)-azetidin-1-yl]-methanone; (Compound #4)

[1-Isobutyl-2-(4-methyl-benzyl)-1H-indol-5-yl]-[3-(4-pyridin-2-yl-piperazin-1-yl)-azetidin-1-yl]-methanone; (Compound #5)

[2-(4-Fluoro-phenyl)-benzooxazol-7-yl]-[3-(4-pyridin-2-yl-piperazin-1-yl)-azetidin-1-yl]-methanone; (Compound #6)

[2-(4-Methoxy-phenyl)-benzooxazol-7-yl]-[3-(4-pyridin-2-yl-piperazin-1-yl)-azetidin-1-yl]-methanone; (Compound #7)

(1-Isobutyl-2-phenoxymethyl-1H-indol-5-yl)-[3-(4-pyridin-2-yl-piperazin-1-yl)-azetidin-1-yl]-methanone; (Compound #9)

[1-(2,2-Dimethyl-propyl)-2-phenyl-1H-indol-5-yl]-[3-(4-pyridin-2-yl-piperazin-1-yl)-azetidin-1-yl]-methanone; (Compound #10)

(1-Cyclohexylmethyl-2-phenoxymethyl-1H-indol-5-yl)-[3-(4-pyridin-2-yl-piperazin-1-yl)-azetidin-1-yl]-methanone; (Compound #11)

(1-Isobutyl-2-phenyl-1H-indol-5-yl)-[3-(4-pyridin-2-yl-piperazin-1-yl)-azetidin-1-yl]-methanone; (Compound #13)

(2-Benzyl-1-cyclohexylmethyl-1H-indol-5-yl)-[3-(4-pyridin-2-yl-piperazin-1-yl)-azetidin-1-yl]-methanone; (Compound #18)

(1-Cyclohexylmethyl-2-propyl-1H-indol-5-yl)-[3-(4-pyridin-2-yl-piperazin-1-yl)-azetidin-1-yl]-methanone; (Compound #28)

and enantiomers, diastereomers, solvates and pharmaceutically acceptable salt thereof.

In another embodiment, the present invention is directed to treating, ameliorating or preventing a disease, syndrome, condition or disorder that is affected by inhibition of MGL, comprising administering to a subject in need thereof, a therapeutically effective amount of a compound selected from the group consisting of (2-Cyclohexyl-benzooxazol-6-yl)-[3-(4-pyridin-2-yl-piperazin-1-yl)-azetidin-1-yl]-methanone; (Compound #2)

[2-(3-Fluoro-phenyl)-benzooxazol-7-yl]-[3-(4-pyridin-2-yl-piperazin-1-yl)-azetidin-1-yl]-methanone; (Compound #3)

[1-Isobutyl-2-(4-methyl-benzyl)-1H-indol-5-yl]-[3-(4-pyridin-2-yl-piperazin-1-yl)-azetidin-1-yl]-methanone; (Compound #5)

[2-(4-Methoxy-phenyl)-benzooxazol-7-yl]-[3-(4-pyridin-2-yl-piperazin-1-yl)-azetidin-1-yl]-methanone; (Compound #7)

[1-(2,2-Dimethyl-propyl)-2-phenyl-1H-indol-5-yl]-[3-(4-pyridin-2-yl-piperazin-1-yl)-azetidin-1-yl]-methanone; (Compound #10)

(1-Cyclohexylmethyl-2-phenoxymethyl-1H-indol-5-yl)-[3-(4-pyridin-2-yl-piperazin-1-yl)-azetidin-1-yl]-methanone; (Compound #11)

(2-Cyclopentylmethyl-1-methyl-1H-indol-5-yl)-[3-(4-pyridin-2-yl-piperazin-1-yl)-azetidin-1-yl]-methanone; (Compound #12)

(1-Isobutyl-2-phenyl-1H-indol-5-yl)-[3-(4-pyridin-2-yl-piperazin-1-yl)-azetidin-1-yl]-methanone; (Compound #13)

(2-Benzyl-1-cyclohexylmethyl-1H-indol-5-yl)-[3-(4-pyridin-2-yl-piperazin-1-yl)-azetidin-1-yl]-methanone; (Compound #18)

[2-(3-Methoxy-phenyl)-benzooxazol-5-yl]-[3-(4-pyridin-2-yl-piperazin-1-yl)-azetidin-1-yl]-methanone; (Compound #20)

(2-Benzyl-1-cyclohexylmethyl-1H-indol-5-yl)-{3-[4-(2-methoxy-phenyl)-piperazin-1-yl]-azetidin-1-yl}-methanone; (Compound #23)

2-Methoxy-1-{5-[3-(4-pyridin-2-yl-piperazin-1-yl)-azetidine-1-carbonyl]-2-p-tolyl-1H-indol-3-yl}-ethanone; (Compound #27)

(1-Cyclohexylmethyl-2-propyl-1H-indol-5-yl)-[3-(4-pyridin-2-yl-piperazin-1-yl)-azetidin-1-yl]-methanone; (Compound #28)

and enantiomers, diastereomers, solvates and pharmaceutically acceptable salt thereof.

In another embodiment, the present invention is directed to treating, ameliorating or preventing a disease, syndrome, condition or disorder that is affected by inhibition of MGL, comprising administering to a subject in need thereof, a therapeutically effective amount of a compound selected from the group consisting of (2-Cyclohexyl-benzooxazol-6-yl)-[3-(4-pyridin-2-yl-piperazin-1-yl)-azetidin-1-yl]-methanone; (Compound #2)

[2-(3-Fluoro-phenyl)-benzooxazol-7-yl]-[3-(4-pyridin-2-yl-piperazin-1-yl)-azetidin-1-yl]-methanone; (Compound #3)

[2-(4-Fluoro-phenyl)-benzooxazol-7-yl]-[3-(4-pyridin-2-yl-piperazin-1-yl)-azetidin-1-yl]-methanone; (Compound #6)

(2-tert-Butyl-benzooxazol-6-yl)-[3-(4-pyridin-2-yl-piperazin-1-yl)-azetidin-1-yl]-methanone; (Compound #19)

and enantiomers, diastereomers, solvates and pharmaceutically acceptable salt thereof.

In another embodiment, the present invention is directed to the use of any single compound or subset of compounds selected from the compounds listed in Tables 1-3 below, or an enantiomer, diastereomer, solvate or pharmaceutically acceptable salt thereof; for the treatment, amelioration or prevention or a disease, syndrome, condition or disorder that is affected by the inhibition of MGL, in a subject in need thereof. The compounds of formula (I) of the present invention are as listed in Tables 1-3, below.

TABLE 1

Compounds of Formula (Ia)

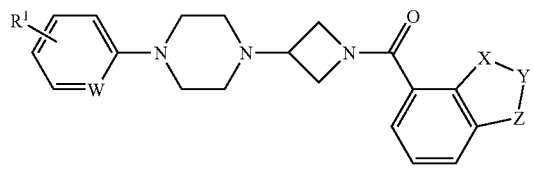

| Cmpd No. | W | R¹ | X—Y—Z | R² |
|---|---|---|---|---|
| 3 | N | H | —O—C(R²)=N— | 3-fluorophenyl |
| 6 | N | H | —O—C(R²)=N— | 4-fluorophenyl |
| 7 | N | H | —O—C(R²)=N— | 4-methoxyphenyl |

TABLE 2

Compounds of Formula (Ib)

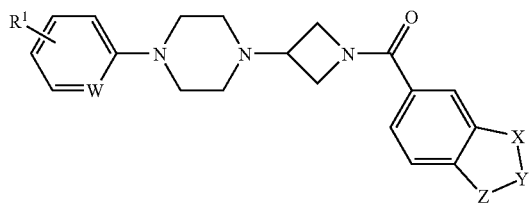

| Cmpd No. | W | R¹ | X—Y—Z | R² | R³ |
|---|---|---|---|---|---|
| 1 | N | H | —CH—C(R²)—N(R³)— | phenoxymethyl | 2,2-dimethylpropyl |
| 2 | N | H | —O—C(R²)=N— | cyclohexyl | |
| 4 | N | H | —CH—C(R²)—N(R³)— | 4-methylphenyl | isobutyl |
| 5 | N | H | —CH—C(R²)—N(R³)— | phenylmethyl | isobutyl |
| 8 | N | H | —CH—C(R²)—N(R³)— | isobutyl | isobutyl |
| 9 | N | H | —CH—C(R²)—N(R³)— | phenoxymethyl | isobutyl |
| 10 | N | H | —CH—C(R²)—N(R³)— | phenyl | 2,2-dimethylpropyl |
| 11 | N | H | —CH—C(R²)—N(R³)— | phenoxymethyl | cyclohexylmethyl |
| 12 | N | H | —CH—C(R²)—N(R³)— | cyclopentylmethyl | methyl |
| 13 | N | H | —CH—C(R²)—N(R³)— | phenyl | isobutyl |
| 14 | N | H | —CH—C(R²)—N(R³)— | cyclohexylmethyl | hydrogen |
| 16 | N | H | —CH—C(R²)—N(R³)— | n-propyl | methyl |
| 17 | CH | 2-methoxy | —CH—C(R²)—N(R³)— | phenoxymethyl | isobutyl |
| 18 | N | H | —CH—C(R²)—N(R³)— | phenylmethyl | cyclohexylmethyl |
| 19 | N | H | —O—C(R²)=N— | t-butyl | |
| 21 | CH | 2-methoxy | —CH—C(R²)—N(R³)— | phenylmethyl | isobutyl |
| 22 | CH | 2-methoxy | —CH—C(R²)—N(R³)— | phenoxymethyl | 2,2-dimethylpropyl |
| 23 | CH | 2-methoxy | —CH—C(R²)—N(R³)— | phenylmethyl | cyclohexylmethyl |
| 24 | CH | 2-methoxy | —CH—C(R²)—N(R³)— | phenyl | 2,2-dimethylpropyl |
| 25 | CH | 4-fluoro | —CH—C(R²)—N(R³)— | phenyl | 2,2-dimethylpropyl |
| 26 | N | H | —CH—C(R²)—N(R³)— | t-butyl | 2,2-dimethypropyl |
| 28 | N | H | —CH—C(R²)—N(R³)— | n-propyl | cyclohexylmethyl |

TABLE 3

Compounds of Formula (Ic)

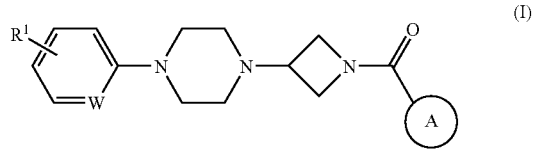

| Cmpd No. | W | R¹ | X—Y—Z | R² | R³ |
|---|---|---|---|---|---|
| 15 | N | H | —O—C(R²)=N— | 2-methoxyphenylmethyl | |
| 20 | N | H | —O—C(R²)=N— | 3-methoxyphenyl | |
| 27 | N | H | —NH—C(R²)=C(R³)— | 4-methylphenyl | methoxymethylcarbonyl |

In an embodiment, the present invention is directed to treating, ameliorating or preventing a disease, syndrome, condition or disorder that is affected by inhibition of MGL, wherein the disease, syndrome, condition or disorder that is affected by inhibition of MGL is selected from the group consisting of inflammatory pain and neuropathic pain; comprising administering to a subject in need thereof (including a mammal and/or human), a therapeutically effective amount of a compound of formula (I)

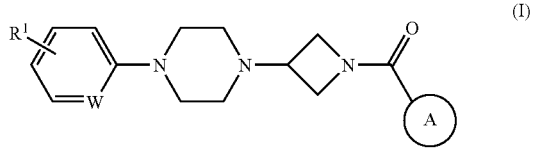

selected from the group as herein defined; and enantiomers, diastereomers, solvates and pharmaceutically acceptable salt thereof.

In an embodiment, the present invention is directed to treating, ameliorating or preventing inflammatory pain; comprising administering to a subject in need thereof (including a mammal and/or human), a therapeutically effective amount of a compound of formula (I)

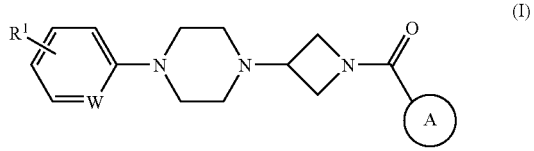

selected from the group as herein defined; and enantiomers, diastereomers, solvates and pharmaceutically acceptable salt thereof. In another embodiment of the present invention, the inflammatory pain is selected from the group consisting of visceral pain and inflammatory hyeralgesia, preferably visceral pain.

In an embodiment, the present invention is directed to treating, ameliorating or preventing inflammatory hyperalgesia, comprising administering to a subject in need thereof (including a mammal and/or human), a therapeutically effective amount of a compound of formula (I)

selected from the group as herein defined; and enantiomers, diastereomers, solvates and pharmaceutically acceptable salt thereof. In another embodiment of the present invention, the inflammatory hyperalgesia is ulcerative colitis.

In an embodiment, the present invention is directed to treating, ameliorating or preventing neuropathic pain, comprising administering to a subject in need thereof (including a mammal and/or human), a therapeutically effective amount of a compound of formula (I)

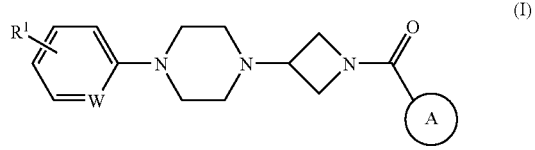

selected from the group as herein defined; and enantiomers, diastereomers, solvates and pharmaceutically acceptable salt thereof. In another embodiment of the present invention, the neuropathic pain is neuropathic cold allodynia.

For use in medicine, salts of compounds of formula (I) refer to non-toxic "pharmaceutically acceptable salts." Other salts may, however, be useful in the preparation of compounds of formula (I) or of their pharmaceutically acceptable salts thereof. Suitable pharmaceutically acceptable salts of compounds of formula (I) include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of formula (I) carry an acidic moiety, suitable pharmaceutically acceptable salts thereof may include alkali metal salts, such as sodium or potassium salts; alkaline earth metal salts, such as calcium or magnesium salts; and salts formed with suitable organic ligands, such as quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases that may be used in the preparation of pharmaceutically acceptable salts include acids such as acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxoglutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Embodiments of the present invention include prodrugs of compounds of formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

Where the processes for the preparation of the compounds according to certain embodiments of the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\%(+)\text{-enantiomer} = \frac{(\text{mass}(+)\text{-enantiomer})}{(\text{mass}(+)\text{-enantiomer}) + (\text{mass}(-)\text{-enantiomer})} \times 100.$$

Another embodiment of the present invention is a composition, including a pharmaceutical composition, comprising, consisting of, and consisting essentially of the (−)-enantiomer of a compound of formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups, such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of formula (I) may be admixed with any suitable binder(s), lubricant(s), suspending agent(s), coating agent(s), solubilizing agent(s), and combinations thereof.

Solid oral dosage forms, such as tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a white wax or white soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example intracavernosally, intravenously, intramuscularly, subcutaneously, intradermally or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of formula (I) can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus for liquid oral preparations, such as suspensions, syrups, elixirs and solutions, suitable carriers, excipients and diluents include water, glycols, oils, alcohols, flavoring agents, preservatives, stabilizers, coloring agents and the like; for solid oral preparations, such as powders, capsules and tablets, suitable carriers, excipients and diluents include starches, sugars, diluents, granulating agents, lubricants, binders, disintegrating agents and the like. Solid oral preparations also may be optionally coated with substances, such as, sugars, or be enterically-coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives, such as solubilizers and preservatives.

A therapeutically effective amount of a compound of formula (I) or a pharmaceutical composition thereof includes a dose range from about 0.1 mg to about 3000 mg, or any amount or range therein, in particular from about 1 mg to about 1000 mg, or any amount or range therein, more particularly, from about 10 mg to about 500 mg, or any amount or range therein, of ingredient compound of formula (I) in a regimen of about 1 to 4 times per day for an average (70 kg) human; although, it is apparent to one skilled in the art that the therapeutically effective amount for a compound of formula (I) will vary as will the diseases, syndromes, conditions, and disorders being treated.

For oral administration, a pharmaceutical composition is preferably provided in the form of tablets containing about 0.01, about 10, about 50, about 100, about 150, about 200, about 250, and about 500 milligrams of a compound of formula (I).

Advantageously, a compound of formula (I) may be administered in a single daily dose, or the total daily dosage may be administered in divided doses of two, three and four times daily.

Optimal dosages of a compound of formula (I) to be administered may be readily determined and will vary with the particular compound used, the mode of administration, the strength of the preparation, and the advancement of the disease, syndrome, condition, or disorder. In addition, factors associated with the particular subject being treated, including subject age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

One skilled in the art will recognize that, both in vivo and in vitro trials using suitable, known and generally accepted cell and/or animal models are predictive of the ability of a test compound to treat or prevent a given disorder. One skilled in the art will further recognize that human clinical trails including first-in-human, dose ranging and efficacy trials, in healthy patients and/or those suffering from a given disorder, may be completed according to methods well known in the clinical and medical arts.

A compound of formula (I) may be administered in any of the foregoing compositions and dosage regimens or by means of those compositions and dosage regimens established in the art whenever use of a compound of formula (I) is required for a subject in need thereof.

General Synthetic Methods

Representative compounds of the present invention may be synthesized in accordance with the general synthetic methods described below and illustrated in the schemes that follow. Since the schemes are an illustration, the invention should not be construed as being limited by the specific chemical reactions and specific conditions described in the schemes and examples. The various starting materials used in the schemes are commercially available or may be prepared by methods well within the skill of persons versed in the art. The variables are as defined herein and within the skill of persons versed in the art.

Abbreviations used in the specification, particularly the Schemes and Examples, are as follows:

| | |
|---|---|
| DCC= | N,N-Dicyclohexylcarbodiimide |
| DCM= | Dichloromethane |
| DIPEA or DIEA= | Diisopropylethylamine |
| DMF= | N,N-Dimethylformamide |
| DMSO= | Dimethylsulfoxide |
| EDTA= | Ethylenediaminetetraacetic acid |
| EtOAc= | Ethyl Acetate |
| HATU= | O-(7-Azabenzotriazol-1-yl)-N,N,N'',N''-Tetramethyl Uronium Hexafluorophosphate |
| HBTU= | O-Benzotriazole-N,N,N',N'-tetramethyl-uronium-hexafluoro-phosphate |
| HEPES= | 4-(2-Hydroxyethyl)-1-piperazineethane sulfonic acid |
| TEA= | Triethylamine |
| TFA= | Trifluoroacetic Acid |
| THF= | Tetrahydrofuran |

The compounds of Formula (I) of the present invention may be prepared according to the process as outlined in Scheme 1, below.

Scheme 1

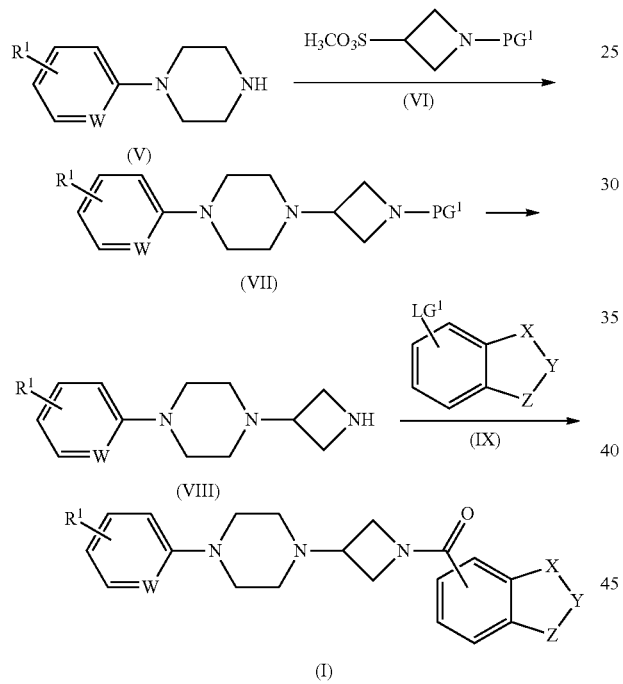

Accordingly, a suitably substituted compound of formula (V), a known compound or compound prepared by known methods, is reacted with a suitably substituted compound of formula (VI), wherein $PG^1$ is a suitably selected nitrogen protecting group such as —CH(phenyl)$_2$, benzyl, t-butyl, methyl, and the like, preferably —CH(phenyl)$_2$, a known compound or compound prepared by known methods; in the presence of an organic base such as DIPEA, pyridine, and the like (preferably not TEA); in an organic solvent such as acetonitrile, THF, DCM, and the like; preferably at a temperature in the range of from about 50° C. to about 90° C.; to yield the corresponding compound of formula (VII).

The compound of formula (VII) is de-protected according to known methods, to yield the corresponding compound of formula (VIII). For example, wherein $PG^1$ is —CH(phenyl)$_2$, the compound of formula (VII) is de-protected by reacting with 1-chloroethyl chloroformate, in an organic solvent such as dichloromethane, and then refluxed in an organic solvent such as methanol, to yield the corresponding compound of formula (VIII).

The compound of formula (VIII) is reacted with a suitably substituted compound of formula (IX), wherein $LG^1$ is selected from the group consisting of —C(O)Cl and C(O)OH, and wherein $LG^1$ is bound at the desired bonding position on benzene ring of the the benzo-fused portion of the compound of formula (IX), a known compound or compound prepared by known methods, in the presence of a suitably selected coupling agent such as HATU, HBTU, DCC, and the like; in the presence of a suitably selected organic base such as DIPEA, TEA, pyridine, and the like; in an organic solvent such as acetonitrile, DMF, DCM, and the like; to yield the corresponding compound of formula (I).

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

(2-Cyclohexyl-benzooxazol-6-yl)-[3-(4-pyridin-2-yl-piperazin-1-yl)-azetidin-1-yl]-methanone

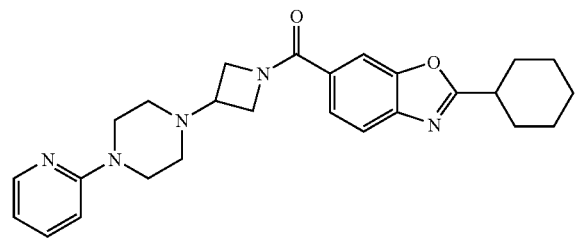 [SMILES: O=C(c1ccc2nc(C3CCCCC3)oc2c1)N1CC(N2CCN(c3ccccn3)CC2)C1]

STEP A: 2-Cyclohexyl-benzooxazole-6-carboxylic acid

To a solution of 4-amino-3-hydroxy-benzoic acid methyl ester (5 g, 29.91 mmol) in CH$_3$OH (150 mL) was added cyclohexanecarbaldehyde (3.6 mL, 29.91 mmol) at room temperature. The resulting mixture was stirred at room temperature for 2 h. The solvent was removed by evaporation and CH$_3$CN (150 mL) was added to the residue. Lead (IV) acetate (13.26 g, 29.91 mmol) was added as one portion under N$_2$ and the resulting mixture was refluxed for 10 min. After cooling, the resulting solid was filtered and washed with CH$_3$CN. To the filtrate was then added 3N NaOH (40 mL). The resulting mixture was stirred at 50° C. for 18 h. The solvent was removed by evaporation and the resulting residue was purified by flash chromatography on silica gel to yield 2-cyclohexyl-benzooxazole-6-carboxylic acid. MS m/z (M+H$^+$) 246.2.

STEP B: (2-Cyclohexyl-benzooxazol-6-yl)-(3-hydroxy-azetidin-1-yl)-methanone

To a solution of 2-cyclohexyl-benzooxazole-6-carboxylic acid (0.47 g, 1.9 mmol) and HBTU (0.94 g, 2.5 mmol) in DMF (10 mL) was added DIPEA (1.4 mL, 7.6 mmol). The resulting mixture was stirred at room temperature for 10 min, and then the hydrochloride salt of azetidin-3-ol (0.452 g, 4.7 mmol) was added. The resulting mixture was stirred at room temperature for 1 h, and then purified by reverse phase liquid chromatography. Fractions containing product were lyophilized to yield (2-cyclohexyl-benzooxazol-6-yl)-(3-hydroxy-azetidin-1-yl)-methanone. MS m/z (M+H$^+$) 301.

STEP C: 2-Cyclohexyl-6-{[3-(4-pyridin-2-ylpiperazin-1-yl)azetidin-1-yl]carbonyl}-1,3-benzoxazole Methanesulfonyl chloride (0.152 mL, 1.9 mmol) was added dropwise to a solution of (2-cyclohexyl-benzooxazol-6-yl)-(3-hydroxy-azetidin-1-yl)-methanone (0.48 g, 1.6 mmol) and DIPEA (0.558 mL, 3.2 mmol) in DCM (20 mL) at −40° C. under nitrogen Immediately following the addition, the cooling bath was removed and the mixture slowly warmed to room temperature. The resulting mixture was then washed with water, dried using magnesium sulfate, filtered, and the solvent removed under reduced pressure. The resulting residue was dissolved in acetonitrile (1 mL). DIPEA (0.41 mL, 2.4 mmol) and N-(2-pyridyl)piperazine (1.6 mmol) were added. The resulting mixture was then microwaved at 160° C. for 4 hours. DMF (3 mL) was added to the resulting mixture, which was then purified by reverse phase liquid chromatography. The fractions containing product were diluted with 1N HCl (5 mL) and then lyophilized to yield 2-cyclohexyl-6-{[3-(4-pyridin-2-ylpiperazin-1-yl)azetidin-1-yl]carbonyl}-1,3-benzoxazole as its corresponding hydrochloride salt.

$^1$H NMR (400 MHz, DMSO-d$_6$) δ=9.21 (s, 1H), 8.15 (d, J=5.1 Hz, 1H), 7.96 (d, J=8.3 Hz, 1H), 7.81 (br. s., 1H), 7.16-7.22 (m, 1H), 7.06 (d, J=8.3 Hz, 1H), 6.88 (s, 1H), 4.54 (br. s., 2H), 4.38 (d, J=6.6 Hz, 2H), 4.13 (br. s., 1H), 3.73 (br. s., 8H), 3.31-3.60 (m, 1H), 1.77 (d, J=13.7 Hz, 4H), 1.65 (br. s., 1H), 1.32-1.44 (m, 2H), 1.15-1.32 (m, 2H), 1.06 (t, J=7.0 Hz, 1H). MS m/z (M+H$^+$) 446.

Compounds #2 through 28 may be similarly prepared according to the procedures as described in Example 1, above and substituting suitably selected and/or substituted reagents, starting materials and purification methods known to those skilled in the art.

Example 2

(In Vitro Assay): MGL Enzyme Activity Assay

All rate-based assays were performed in black 384-well polypropylene PCR microplates (Abgene) in a total volume of 30 μL. Substrate 4-methylumbelliferyl butyrate (4MU-B, Sigma) and purified mutant MGL enzyme (mut-MGLL 11-313 L179S L186S) were diluted separately into 20 mM PIPES buffer (pH 7), containing 150 mM NaCl, and 0.001% Tween 20. Compounds of Formula (I) were pre-dispensed (50 nL) into the assay plate using a Cartisian Hummingbird (Genomic Solutions, Ann Arbor, Mich.) prior to adding 4MU-B (25 μL of 1.2× solution, final concentration of 10 μM) followed by enzyme (5 μL of a 6× solution, final concentration of 5 nM) to initiate the reaction. Final compound concentrations ranged from 17 to 0.0003 μM. The fluorescence change due to 4MU-B cleavage was monitored with excitation and emission wavelengths of 335 and 440 nm, respectively, and a bandwidth of 10 nm (Safire$^2$, Tecan) at 37° C. for 5 min.

The IC$_{50}$ values for compounds of Formula (I) were determined using Excel from a fit of the equation to the concentration-response-plot of the fractional activity as a function of inhibitor concentration.

Example 3

(In Vitro Assay): MGL ThermoFluor® Assay

The ThermoFluor (TF) assay is a 384-well plate-based binding assay that measures thermal stability of proteins (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. *J Biomol Screen* 2001, 6, 429-40; Matulis, D., Kranz, J. K., Salemme, F. R., and Todd, M. J. *Biochemistry* 2005, 44, 5258-66). The experiments were carried out using instruments available from Johnson & Johnson Pharmaceutical Research & Development, LLC. TF dye used in all experiments was 1,8-ANS (Invitrogen: A-47). Final TF assay conditions used for MGL studies were 0.07 mg/ml of purified mutant MGL (mut-MGLL 11-313 L179S L186S), 100 μM ANS, 200 mM NaCl, 0.001% Tween-20 in 50 mM PIPES (pH=7.0).

Screening compound plates contained 100% DMSO compound solutions at a single concentration. For follow-up concentration-response studies, compounds were arranged in a pre-dispensed plate (Greiner Bio-one: 781280), wherein compounds were serially diluted in 100% DMSO across 11 columns within a series. Columns 12 and 24 were used as DMSO reference and contained no compound. For both single and multiple compound concentration-response experiments, the compound aliquots (50 nL) were robotically pre-dispensed directly into black 384-well polypropylene PCR microplates (Abgene: TF-0384/k) using the Cartesian Hummingbird liquid handler (Genomic Solutions, Ann Arbor, Mich.). Following compound dispense, protein and dye solutions were added to achieve the final assay volume of 3 μL. The assay solutions were overlayed with 1 μL of silicone oil (Fluka, type DC 200: 85411) to prevent evaporation.

Bar-coded assay plates were robotically loaded onto a thermostatically controlled PCR-type thermal block and then heated from 40 to 90° C. degrees at a ramp-rate of 1° C./min for all experiments. Fluorescence was measured by continuous illumination with UV light (Hamamatsu LC6) supplied via fiber optics and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. A single image with 20-sec exposure time was collected at each temperature, and the sum of the pixel intensity in a given area of the assay plate was recorded versus temperature and fit to standard equations to yield the T$_m$. (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R., *J Biomol Screen* 2001, 6, 429-40).

Example 4

2-AG Accumulation Assay

HeLa cells were homogenated with a Polytron in 10 ml (about 400 million cells) HEPES buffer (HEPES 20 mM, pH 7.4, NaCl 125 mM, EDTA 1 mM, KCl 5 mM, Glucose 20 mM). The homogenate from 20 million cells (0.5 ml) was incubated with MGL inhibitor for 15 min to block MGL activity and then the HEPES buffer solution was incubated with calcium (10 mM) for 20 min. The total reaction volume was 5 ml. The reactions were stopped by 6 mL organic solvent extraction (2:1 chloroform/methanol). Methoxy arachidonyl fluorophosphonate (MAFP) was used as positive control. In the absence of MAFP the 2-AG levels are about 3.4 pmol/sample. In the presence of 100 nM MAFP 2-AG levels increase to 174 pmol/sample. Accumulated 2-AG in the organic phase was measured by a HPLC/MS method, according to the following equation: % MAFP=(Compound 2-AG/MAFP 2-AG)×100.

Representative compounds of formula (I) were tested according to the procedure as described in Example 2, 3 and 4 above, with results as listed in Table 4.

TABLE 4

| Cmpd No. | Example 2 IC$_{50}$ (μM) | Example 3 K$_d$ (μM) | Example 4 % MAFP @ 1 μM | Example 4 % MAFP @ 10 μM |
| --- | --- | --- | --- | --- |
| 1  | 0.031 | 0.001  |      |       |
| 2  | 0.050 | 0.130  | 39.7 | 87.6  |
| 3  | 0.055 | 0.091  | 45.7 | 82.9  |
| 4  | 0.060 | 0.002  |      |       |
| 5  | 0.077 | 0.008  |      | 82.9  |
| 6  | 0.100 | 0.048  | 30.6 | 68.8  |
| 7  | 0.186 | 0.083  |      | 79.5  |
| 8  | 0.220 | 0.330  |      | 72.9  |
| 9  | 0.230 | 0.040  |      | 67.8  |
| 10 | 0.330 | 0.020  |      | 160.1 |
| 11 | 0.350 | 0.010  |      | 160.1 |
| 12 | 0.360 | 5.000  |      | 142.0 |
| 13 | 0.430 | 0.030  |      | 93.5  |
| 14 | 0.440 | 5.000  |      | 53.7  |
| 15 | 0.470 | 1.850  |      | 57.6  |
| 16 | 0.810 | 4.550  |      | 61.1  |
| 17 | 0.880 | 4.000  |      | 25.9  |
| 18 | 0.920 | 0.050  |      | 134.6 |
| 19 | 1.073 | 0.172  | 19.9 | 47.3  |
| 20 | 1.340 | 5.560  |      | 86.9  |
| 21 | 1.420 | 6.670  |      | 29.2  |
| 22 | 1.670 | 5.560  |      | 50.1  |
| 23 | 1.890 | 2.500  |      | 84.5  |
| 24 | 1.980 | 5.000  |      | 58.8  |
| 25 | 3.810 | 6.670  |      | 65.8  |
| 26 | 5.460 | 11.110 |      | 37.0  |
| 27 | 9.441 | 28.569 |      | 76.3  |
| 28 |       | 0.090  |      | 77.0  |

Example 5

Oral Formulation—Prophetic Example

As a specific embodiment of an oral composition, 100 mg of the compound #1, prepared as in Example 1 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method of treating or ameliorating a disease, syndrome, condition or disorder that is affected by the inhibition of MGL, wherein the disease, syndrome, condition or disorder is selected from the group consisting of pain, inflammatory pain, and neuropathic pain, comprising administering to a subject in need thereof, a therapeutically effective amount of a compound of formula (I)

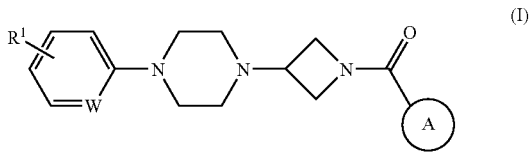

selected from the group consisting of a compound wherein W is N, $R^1$ is H,

is

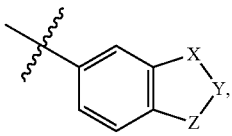

X—Y—Z is —CH═C($R^2$)—N($R^3$)—, $R^2$ is phenoxymethyl, and $R^3$ is 2,2-dimethylpropyl;

a compound wherein W is N, $R^1$ is H,

is

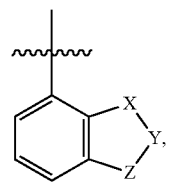

X—Y—Z is —O—C($R^2$)═N—, and $R^2$ is 3-fluorophenyl;

a compound wherein W is N, $R^1$ is H,

is

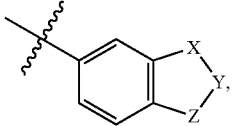

X—Y—Z is —CH═C($R^2$)—N($R^3$)—, $R^2$ is 4-methylphenyl, and $R^3$ is isobutyl;

a compound wherein W is N, $R^1$ is H,

is

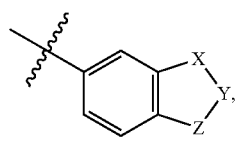

X—Y—Z is —CH—C($R^2$)—N($R^3$)—, $R^2$ is phenylmethyl, and $R^3$ is isobutyl;
  a compound wherein W is N, $R^1$ is H,

is

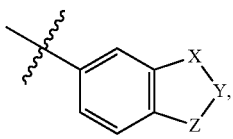

X—Y—Z is —O—C($R^2$)=N—, and $R^2$ is 4-fluorophenyl;
  a compound wherein W is N, $R^1$ is H,

is

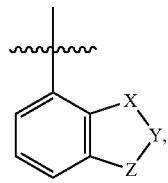

X—Y—Z is —O—C($R^2$)=N—, and $R^2$ is 4-methoxyphenyl;
  a compound wherein W is N, $R^1$ is H,

is

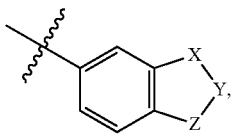

X—Y—Z is —CH—C($R^2$)—N($R^3$)—, $R^2$ is isobutyl, and $R^3$ is isobutyl;
  a compound wherein W is N, $R^1$ is H,

is

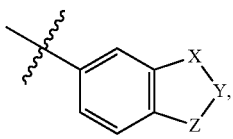

X—Y—Z is —CH—C($R^2$)—N($R^3$)—, $R^2$ is phenoxymethyl, and $R^3$ is isobutyl;
  a compound wherein W is N, $R^1$ is H,

is

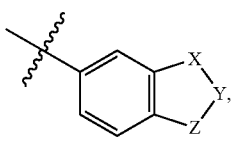

X—Y—Z is —CH—C($R^2$)—N($R^3$)—, $R^2$ is phenyl, and $R^3$ is 2,2-dimethylpropyl;
  a compound wherein W is N, $R^1$ is H,

is

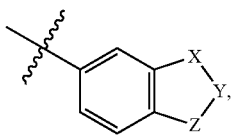

X—Y—Z is —CH—C($R^2$)—N($R^3$)—, $R^2$ is phenoxymethyl, and $R^3$ is cyclohexylmethyl;

a compound wherein W is N, R¹ is H,

is

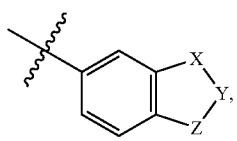

X—Y—Z is —CH—C(R²)—N(R³)—, R² is cyclopentylmethyl, and R³ is methyl;
  a compound wherein W is N, R¹ is H,

is

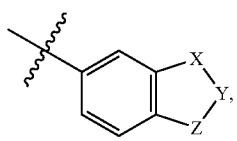

X—Y—Z is —CH—C(R²)—N(R³)—, R² is phenyl, and R³ is isobutyl;
  a compound wherein W is N, R¹ is H,

is

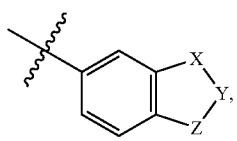

X—Y—Z is —CH—C(R²)—N(R³)—, R² is cyclohexylmethyl, and R³ is hydrogen;
  a compound wherein W is N, R¹ is H,

is

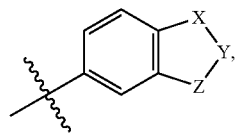

X—Y—Z is —O—C(R²)=N—, and R² is 2-methoxyphenylmethyl;
  a compound wherein W is N, R¹ is H,

is

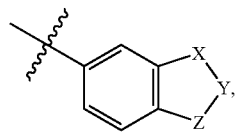

X—Y—Z is —CH—C(R²)—N(R³)—, R² is n-propyl, and R³ is methyl;
  a compound wherein W is CH, R¹ is 2-methoxy,

is

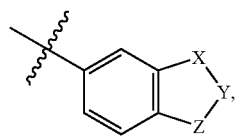

X—Y—Z is —CH—C(R²)—N(R³)—, R² is phenoxymethyl, and R³ is isobutyl;
  a compound wherein W is N, R¹ is H,

is

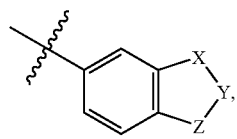

X—Y—Z is —CH—C(R²)—N(R³)—, R² is phenylmethyl, and R³ is cyclohexylmethyl;

a compound wherein W is N, R¹ is H,

is

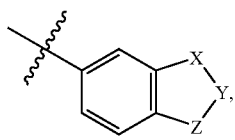

X—Y—Z is —O—C(R²)=N—, and R² is t-butyl;

a compound wherein W is N, R¹ is H,

is

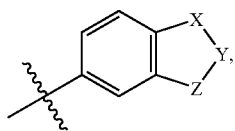

X—Y—Z is —O—C(R²)=N—, and R² is 3-methoxyphenyl;

a compound wherein W is CH, R¹ is 2-methoxy,

is

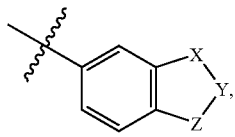

X—Y—Z is —CH—C(R²)—N(R³)—, R² is phenylmethyl, and R³ is isobutyl;

a compound wherein W is CH, R¹ is 2-methoxy,

is

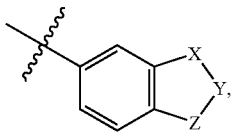

X—Y—Z is —CH—C(R²)—N(R³)—, R² is phenoxymethyl, and R³ is 2,2-dimethylpropyl;

a compound wherein W is CH, R¹ is 2-methoxy,

is

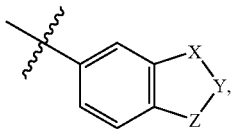

X—Y—Z is —CH—C(R²)—N(R³)—, R² is phenylmethyl, and R³ is cyclohexylmethyl;

a compound wherein W is CH, R¹ is 2-methoxy,

is

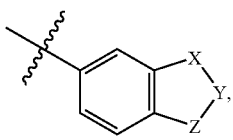

X—Y—Z is —CH—C(R²)—N(R³)—, R² is phenyl, and R³ is 2,2-dimethylpropyl;

a compound wherein W is CH, R¹ is 4-fluoro,

is

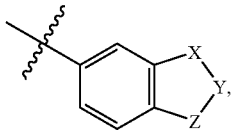

X—Y—Z is —CH—C(R²)—N(R³)—, R² is phenyl, and R³ is 2,2-dimethylpropyl;

a compound wherein W is N, R¹ is H,

is

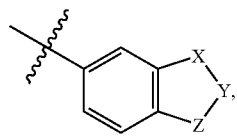

X—Y—Z is —CH—C(R²)—N(R³)—, R² is t-butyl, and R³ is 2,2-dimethylpropyl;

a compound wherein W is N, R¹ is H,

is

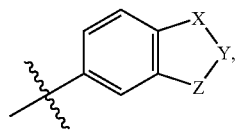

X—Y—Z is —NH—C(R²)—C(R³)—, R² is 4-methylphenyl and R³ is methoxy-methyl-carbonyl;

a compound wherein W is N, R¹ is H,

is

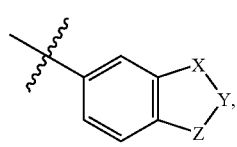

X—Y—Z is —CH—C(R²)—N(R³), R² is n-propyl and R³ is cyclohexylmethyl;

and enantiomers, diastereomers and pharmaceutically acceptable salts thereof.

2. A method as in claim 1, wherein the compound of formula (I) is selected form the group consisting of a compound wherein W is N, R¹ is H,

is

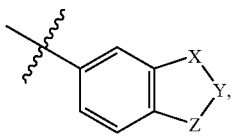

X—Y—Z is —CH—C(R²)—N(R³)—, R² is phenoxymethyl, and R³ is 2,2-dimethylpropyl;

a compound wherein W is N, R¹ is H,

is

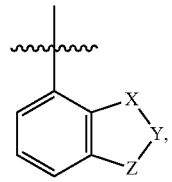

X—Y—Z is —O—C(R²)=N—, and R² is 3-fluorophenyl;

a compound wherein W is N, R¹ is H,

is

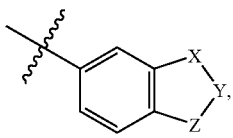

X—Y—Z is —CH—C(R²)—N(R³)—, R² is 4-methylphenyl, and R³ is isobutyl;

a compound wherein W is N, R¹ is H,

is

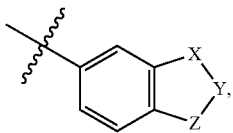

X—Y—Z is —CH—C(R²)—N(R³)—, R² is phenylmethyl, and R³ is isobutyl;

a compound wherein W is N, R¹ is H,

is

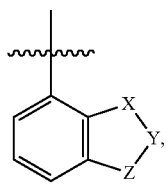

X—Y—Z is —O—C(R²)═N—, and R² is 4-fluorophenyl;
a compound wherein W is N, R¹ is H,

is

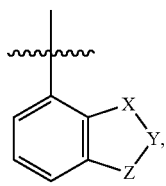

X—Y—Z is —O—C(R²)═N—, and R² is 4-methoxyphenyl;
a compound wherein W is N, R¹ is H,

is

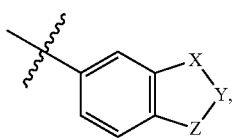

X—Y—Z is —CH═C(R²)—N(R³)—, R² is isobutyl, and R³ is isobutyl;
a compound wherein W is N, R¹ is H,

is

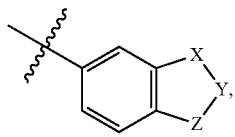

X—Y—Z is —CH═C(R²)—N(R³)—, R² is phenoxymethyl, and R³ is isobutyl;
a compound wherein W is N, R¹ is H,

is

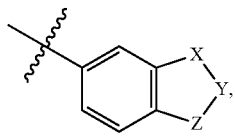

X—Y—Z is —CH═C(R²)—N(R³)—, R² is phenyl, and R³ is 2,2-dimethylpropyl;
a compound wherein W is N, R¹ is H,

is

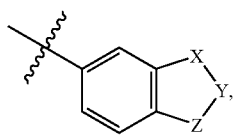

X—Y—Z is —CH═C(R²)—N(R³)—, R² is phenoxymethyl, and R³ is cyclohexylmethyl;
a compound wherein W is N, R¹ is H,

is

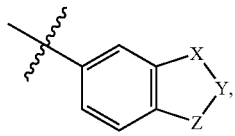

X—Y—Z is —CH═C(R²)—N(R³)—, R² is cyclopentylmethyl, and R³ is methyl;

a compound wherein W is N, R¹ is H,

A is

[structure: benzene ring fused with X-Y-Z]

X—Y—Z is —CH—C(R²)—N(R³)—, R² is phenyl, and R³ is isobutyl;

a compound wherein W is N, R¹ is H,

A is

[structure: benzene ring fused with X-Y-Z]

X—Y—Z is —CH—C(R²)—N(R³)—, R² is cyclohexylmethyl, and R³ is hydrogen;

a compound wherein W is N, R¹ is H,

A is

[structure: benzene ring fused with X-Y-Z]

X—Y—Z is —O—C(R²)=N—, and R² is 2-methoxyphenylmethyl;

a compound wherein W is N, R¹ is H,

A is

[structure: benzene ring fused with X-Y-Z]

X—Y—Z is —CH—C(R²)—N(R³)—, R² is n-propyl, and R³ is methyl;

a compound wherein W is CH, R¹ is 2-methoxy,

A is

[structure: benzene ring fused with X-Y-Z]

X—Y—Z is —CH—C(R²)—N(R³)—, R² is phenoxymethyl, and R³ is isobutyl;

a compound wherein W is N, R¹ is H,

A is

[structure: benzene ring fused with X-Y-Z]

X—Y—Z is —CH—C(R²)—N(R³)—, R² is phenylmethyl, and R³ is cyclohexylmethyl;

and enantiomers, diastereomers and pharmaceutically acceptable salts thereof.

3. A method as in claim 1, wherein the compound of formula (I) is selected form the group consisting of a compound wherein W is N, R¹ is H,

A is

[structure: benzene ring fused with X-Y-Z]

X—Y—Z is —CH—C(R²)—N(R³)—, R² is phenoxymethyl, and R³ is 2,2-dimethylpropyl;

a compound wherein W is N, R¹ is H,

is

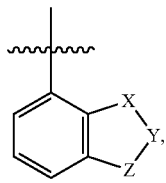

X—Y—Z is —O—C(R²)=N—, and R² is 3-fluorophenyl;
a compound wherein W is N, R¹ is H,

is

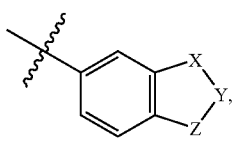

X—Y—Z is —CH—C(R²)—N(R³)—, R² is 4-methylphenyl, and R³ is isobutyl;
a compound wherein W is N, R¹ is H,

is

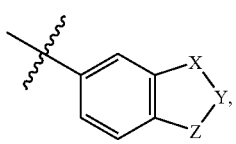

X—Y—Z is —CH—C(R²)—N(R³)—, R² is phenylmethyl, and R³ is isobutyl;
a compound wherein W is N, R¹ is H,

is

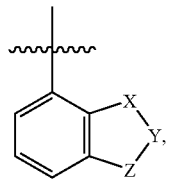

X—Y—Z is —O—C(R²)=N—, and R² is 4-fluorophenyl;
a compound wherein W is N, R¹ is H,

is

X—Y—Z is —O—C(R²)=N—, and R² is 4-methoxyphenyl;
a compound wherein W is N, R¹ is H,

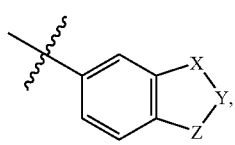

is

X—Y—Z is —CH—C(R²)—N(R³)—, R² is phenoxymethyl, and R³ is isobutyl;
a compound wherein W is N, R¹ is H,

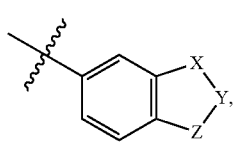

is

X—Y—Z is —CH—C(R²)—N(R³)—, R² is phenyl, and R³ is 2,2-dimethylpropyl;

a compound wherein W is N, R¹ is H,

is

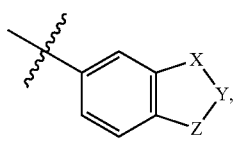

X—Y—Z is —CH═C(R²)—N(R³)—, R² is phenoxymethyl, and R³ is cyclohexylmethyl;

a compound wherein W is N, R¹ is H,

is

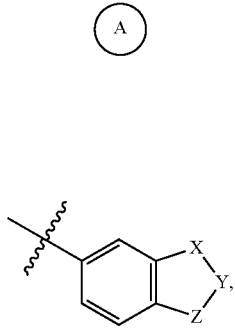

X—Y—Z is —CH═C(R²)—N(R³)—, R² is phenyl, and R³ is isobutyl;

a compound wherein W is N, R¹ is H,

is

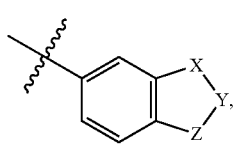

X—Y—Z is —CH═C(R²)—N(R³)—, R² is phenylmethyl, and R³ is cyclohexylmethyl;

a compound wherein W is N, R¹ is H,

is

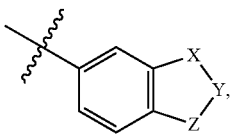

X—Y—Z is —CH═C(R²)—N(R³)—, R² is n-propyl and R³ is cyclohexylmethyl;

and enantiomers, diastereomers and pharmaceutically acceptable salts thereof.

4. A method as in claim 1, wherein the compound of formula (I) is selected form the group consisting of a compound wherein W is N, R¹ is H,

is

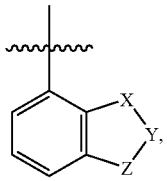

X—Y—Z is —O—C(R²)═N—, and R² is 3-fluorophenyl;

a compound wherein W is N, R¹ is H,

is

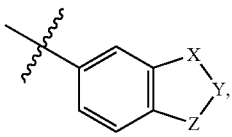

X—Y—Z is —CH═C(R²)—N(R³)—, R² is phenylmethyl, and R³ is isobutyl;

a compound wherein W is N, R¹ is H,

is

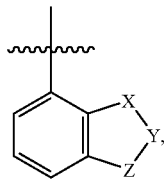

X—Y—Z is —O—C(R$^2$)=N—, and R$^2$ is 4-methoxyphenyl;
a compound wherein W is N, R$^1$ is H,

is

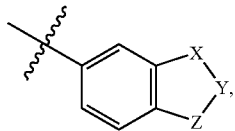

X—Y—Z is —CH—C(R$^2$)—N(R$^3$)—, R$^2$ is phenyl, and R$^3$ is 2,2-dimethylpropyl;
a compound wherein W is N, R$^1$ is H,

is

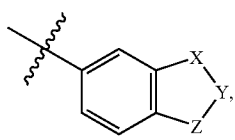

X—Y—Z is —CH—C(R$^2$)—N(R$^3$)—, R$^2$ is phenoxymethyl, and R$^3$ is cyclohexylmethyl;
a compound wherein W is N, R$^1$ is H,

is

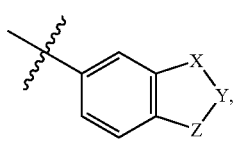

X—Y—Z is —CH—C(R$^2$)—N(R$^3$)—, R$^2$ is cyclopentylmethyl, and R$^3$ is methyl;

a compound wherein W is N, R$^1$ is H,

is

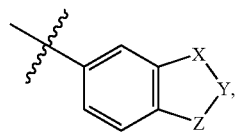

X—Y—Z is —CH—C(R$^2$)—N(R$^3$)—, R$^2$ is phenyl, and R$^3$ is isobutyl;
a compound wherein W is N, R$^1$ is H,

is

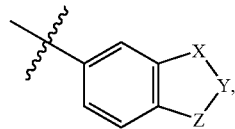

X—Y—Z is —CH—C(R$^2$)—N(R$^3$)—, R$^2$ is phenylmethyl, and R$^3$ is cyclohexylmethyl;
a compound wherein W is N, R$^1$ is H,

is

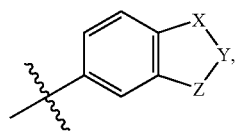

X—Y—Z is —O—C(R$^2$)=N—, and R$^2$ is 3-methoxyphenyl;
a compound wherein W is CH, R$^1$ is 2-methoxy,

is

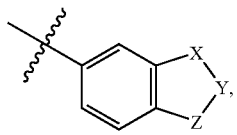

X—Y—Z is —CH—C(R²)—N(R³)—, R² is phenylmethyl, and R³ is cyclohexylmethyl;

a compound wherein W is N, R¹ is H, (A)

is

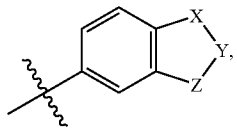

X—Y—Z is —NH—C(R²)—C(R³)—, R² is 4-methylphenyl and R³ is methoxy-methyl-carbonyl;

a compound wherein W is N, R¹ is H, (A)

is

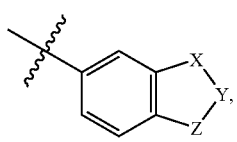

X—Y—Z is —CH—C(R²)—N(R³), R² is n-propyl and R³ is cyclohexylmethyl;

and enantiomers, diastereomers and pharmaceutically acceptable salts thereof.

5. A method as in claim 1, wherein the compound of formula (I) is selected form the group consisting of a compound wherein W is N, R¹ is H, (A)

is

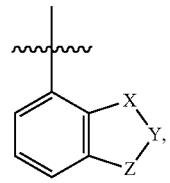

X—Y—Z is —O—C(R²)=N—, and R² is 3-fluorophenyl; a compound wherein W is N, R¹ is H, (A)

is

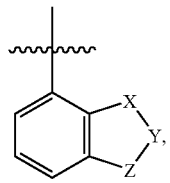

X—Y—Z is —O—C(R²)=N—, and R² is 4-fluorophenyl; a compound wherein W is N, R¹ is H, (A)

is

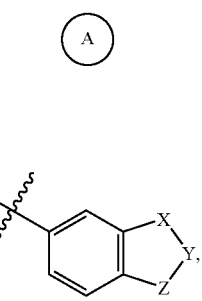

X—Y—Z is —O—C(R²)=N—, and R² is t-butyl;

and enantiomers, diastereomers and pharmaceutically acceptable salts thereof.

6. A method as in claim 1, wherein the disease, syndrome, condition or disorder that is affected by inhibition of MGL is pain.

7. A method as in claim 1, wherein the disease, syndrome, condition or disorder that is affected by inhibition of MGL is inflammatory pain.

8. A method as in claim 1, wherein the disease, syndrome, condition or disorder that is affected by inhibition of MGL is visceral pain.

9. A method as in claim 1, wherein the disease, syndrome, condition or disorder that is affected by inhibition of MGL is neuropathic pain.

10. A method as in claim 1, wherein the disease, syndrome, condition or disorder that is affected by inhibition of MGL is neuropathic cold allodynia.

11. A method as in claim 1, wherein the disease, syndrome, condition or disorder that is affected by inhibition of MGL is selected from the group consisting of inflammatory pain and neuropathic pain.

* * * * *